United States Patent
Lyons

(10) Patent No.: US 10,108,316 B2
(45) Date of Patent: Oct. 23, 2018

(54) COGNITIVE LOAD ASSESSMENT FOR DIGITAL DOCUMENTS

(75) Inventor: Kenton M. Lyons, Santa Clara, CA (US)

(73) Assignee: Intel Corporation, Santa Clara, CA (US)

(*) Notice: Subject to any disclaimer, the term of this patent is extended or adjusted under 35 U.S.C. 154(b) by 777 days.

(21) Appl. No.: 13/995,514

(22) PCT Filed: Dec. 30, 2011

(86) PCT No.: PCT/US2011/068012
§ 371 (c)(1),
(2), (4) Date: Jun. 19, 2013

(87) PCT Pub. No.: WO2013/101143
PCT Pub. Date: Jul. 4, 2013

(65) Prior Publication Data
US 2014/0208226 A1    Jul. 24, 2014

(51) Int. Cl.
*G06F 3/0481* (2013.01)
*G06F 3/0482* (2013.01)
(Continued)

(52) U.S. Cl.
CPC .......... *G06F 3/0484* (2013.01); *A61B 5/16* (2013.01); *G06F 3/013* (2013.01);
(Continued)

(58) Field of Classification Search
CPC ............. G06F 9/4443; G06F 3/0481; H04L 29/08072; G06Q 10/10; H04N 21/4532
See application file for complete search history.

(56) References Cited

U.S. PATENT DOCUMENTS 6,090,051 A * 7/2000 Marshall .............. A61B 5/16
                                                        351/210
6,280,198 B1 * 8/2001 Calhoun .............. A61B 5/16
                                                        434/236
(Continued)

FOREIGN PATENT DOCUMENTS

| CN | 101044470 | 9/2007 |
|----|-----------|--------|
| CN | 102245085 | 11/2011 |
| WO | 02082229 | 10/2002 |

OTHER PUBLICATIONS

Korean Patent Office, English Translation of the Notice of Preliminary Rejection and Office Action, dated Apr. 8, 2015 in Korean Application No. 2014-7017933, 3 pages.
(Continued)

*Primary Examiner* — Kevin L Young
*Assistant Examiner* — Erik V Stitt
(74) *Attorney, Agent, or Firm* — Trop, Pruner & Hu, P.C.

(57) ABSTRACT

An embodiment of the invention includes a system that tracks a user's pupillary response to content located on a web page. The system then determines a cognitive load for the user that is based on the measured response. Cognitive load refers to the total amount of mental activity imposed on working memory in any one instant. Further, the system may aggregate the cognitive load data for one user over time, for many different users, and/or for many different users over time. The cognitive load may be determined for different portions of a displayed page, such as a document object model (DOM) included on the page. The cognitive load may be specified for different elements that make up the DOM. Also, cognitive load may be apportioned over several different DOM elements at one moment in time or over a period of time. Other embodiments are described herein.

11 Claims, 5 Drawing Sheets

(51) Int. Cl.
*G06F 3/0483* (2013.01)
*G06Q 10/10* (2012.01)
*G06F 3/0484* (2013.01)
*G06Q 30/02* (2012.01)
*G06K 9/00* (2006.01)
*A61B 5/16* (2006.01)
*G06F 3/01* (2006.01)
*G06F 17/30* (2006.01)
*A61B 3/11* (2006.01)
*A61B 3/113* (2006.01)

(52) U.S. Cl.
CPC ... *G06F 17/30905* (2013.01); *G06K 9/00442* (2013.01); *G06Q 30/0201* (2013.01); *A61B 3/112* (2013.01); *A61B 3/113* (2013.01); *A61B 2503/24* (2013.01)

(56) References Cited

U.S. PATENT DOCUMENTS

| | | | |
|---|---|---|---|
| 6,526,159 B1 | 2/2003 | Nickerson | |
| 7,645,140 B2* | 1/2010 | Duffy | A61B 5/16 434/236 |
| 7,881,493 B1* | 2/2011 | Edwards | G06K 9/00597 348/78 |
| 8,108,800 B2* | 1/2012 | Kantamneni | G06Q 30/02 351/223 |
| 8,510,166 B2* | 8/2013 | Neven | A61B 3/113 705/14.68 |
| 9,055,905 B2* | 6/2015 | Watkins | A61B 5/18 |
| 2002/0192624 A1* | 12/2002 | Darby | A61B 5/16 434/236 |
| 2003/0181793 A1* | 9/2003 | Buschke | A61B 5/16 600/300 |
| 2003/0222890 A1* | 12/2003 | Salesin | G06F 17/30017 345/629 |
| 2004/0098462 A1* | 5/2004 | Horvitz | G05B 19/404 709/207 |
| 2004/0175683 A1* | 9/2004 | Duffy | A61B 5/16 434/258 |
| 2006/0110008 A1* | 5/2006 | Vertegaal | G06K 9/00604 382/103 |
| 2007/0066916 A1* | 3/2007 | Lemos | A61B 3/113 600/558 |
| 2007/0150827 A1* | 6/2007 | Singh | G06F 3/011 715/773 |
| 2007/0218439 A1* | 9/2007 | Delahunt | G09B 23/28 434/236 |
| 2007/0234202 A1* | 10/2007 | Lyness | G06F 3/0482 715/234 |
| 2007/0282566 A1* | 12/2007 | Whitlow | G06Q 10/06 702/182 |
| 2009/0024964 A1* | 1/2009 | Kantamneni | G06Q 30/02 715/854 |
| 2009/0146775 A1* | 6/2009 | Bonnaud | G06F 9/4446 340/3.1 |
| 2009/0319459 A1* | 12/2009 | Breazeal | G06N 3/004 706/46 |
| 2010/0039618 A1 | 2/2010 | De Lemos | |
| 2010/0092929 A1* | 4/2010 | Hallowell | G09B 7/00 434/167 |
| 2010/0196861 A1 | 8/2010 | Lunner | |
| 2010/0217097 A1* | 8/2010 | Chen | A61B 5/16 600/301 |
| 2010/0295774 A1 | 11/2010 | Hennessey | |
| 2011/0207099 A1 | 8/2011 | Chen | |
| 2013/0128364 A1* | 5/2013 | Wheeler | A61B 3/113 359/630 |
| 2013/0152001 A1* | 6/2013 | Lovitt | G06F 9/4443 715/765 |

OTHER PUBLICATIONS

Le Hégaret, Philippe, "The W3C Document Object Model (DOM)", The W3C, Jul. 26, 2002, 1 page.
Baymer, David, et al., "WebGazeAnalyzer: A System for Capturing and Analyzing Web Reading Behavior Using Eye Gaze" IBM Almaden Research Center, CHI 2005, pp. 1-10.
Le Hégaret, Philippe, "What is the Document Object Model?" W3, Nov. 13, 2000, 6 pages.
Olsen, Anneli, "An Introduction to Eye Tracking: Part 6—Pupil size, blinking and head movement" Tobii Technology's Blog, Jul. 23, 2010, 2 pages.
Ning Zhong, et al., "The impact of different forms of statistical information on reading efficiency, effect, and mental workload: An eye-tracking study", Complex Medical Engineering (CME), 2011 IEEE/ICME International Conference on, IEEE, May 22, 2011 (May 22, 2011), pp. 97-102, XP031993553 DOI:10.1109CCME.2011.5876712 ISBN: 978-1-4244-9323-4.
European Patent Office, Extended Search Report dated Jul. 23, 2015, in European Patent Application No. 11879131.8.
International Searching Authority, "Notification of Transmittal of the International Search Report and the Written Opinion of the International Searching Authority," dated Jul. 10, 2014, in International application No. PCT/US2011/068012.
State Intellectual Property Office, P.R. China, Office Action dated Feb. 16, 2016 in Chinese Patent Application No. 201180076146.9.
State Intellectual Property of The People's Republic of China, Second Office Action dated Sep. 30. 2016, in Chinese Patent Application No. 201180076146.9.
State Intellectual Property of The People's Republic of China, Third Office Action dated Feb. 17, 2017, in Chinese Patent Application No. 201180076146.9.

* cited by examiner

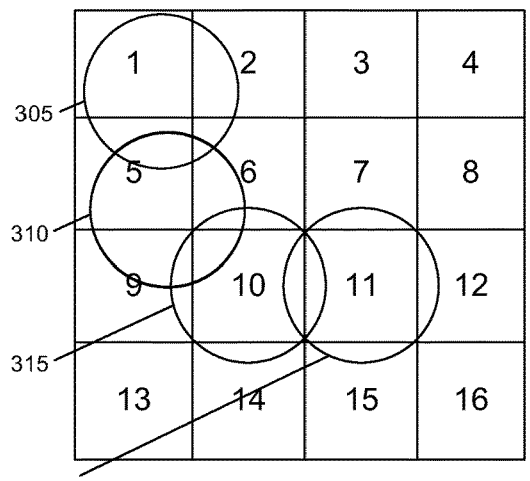

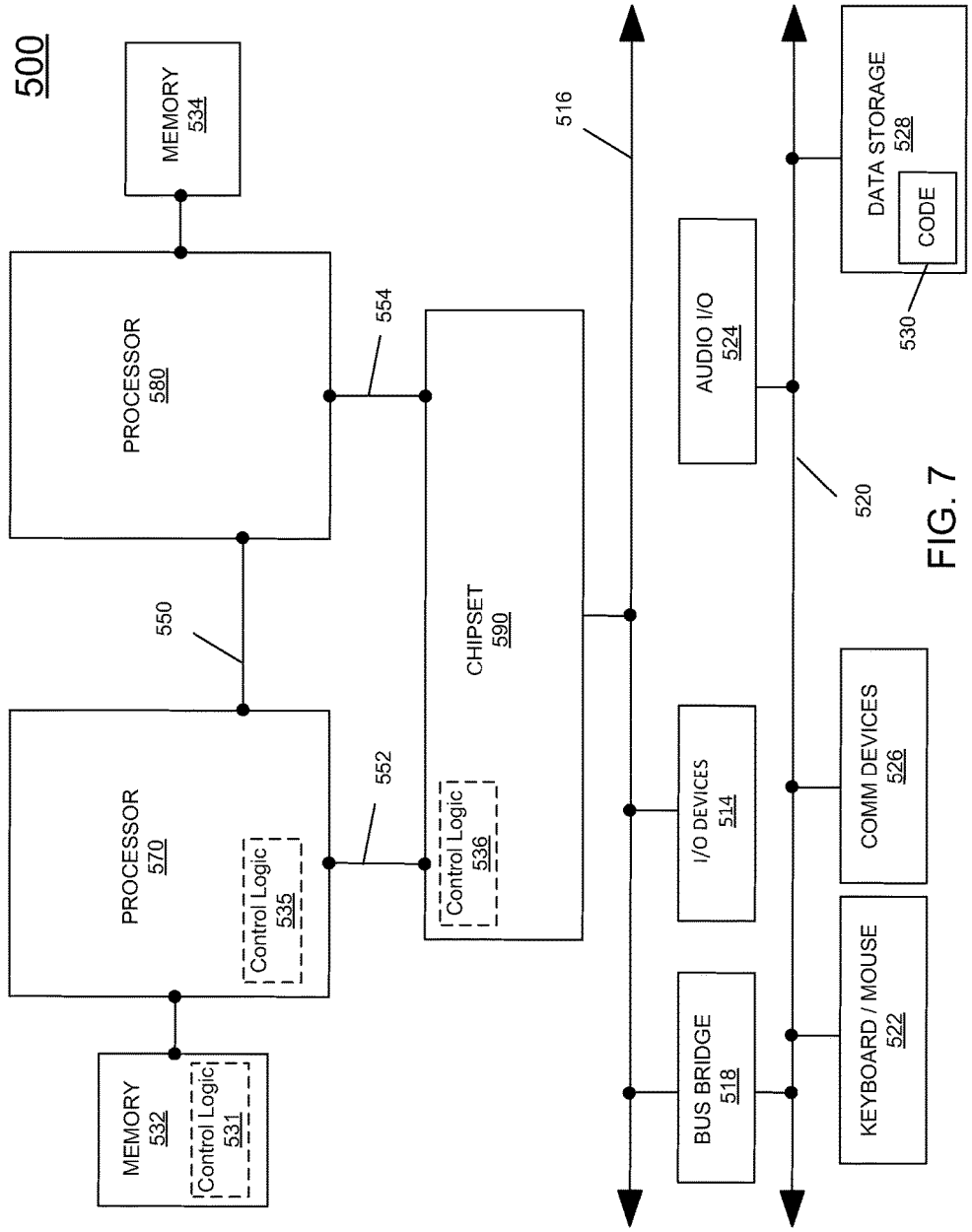

COGNITIVE LOAD ASSESSMENT FOR DIGITAL DOCUMENTS

BACKGROUND

The advent of the web has resulted in a large amount of information being shared electronically with many people. Gaze trackers are used to help determine how users interact with this information. More specifically, gaze trackers are systems that track the "gaze" of a user that is viewing a display. For example, gaze trackers analyze a user's eyes to determine if a user is looking at the top of a web page, the bottom of web page, and so on. More generally, gaze trackers are used to collect data about how users look at information presented to them.

In the context of the web, researchers conduct user studies to generate "heat maps" that represent an aggregation of where the users in the study commonly look. These maps may help an analyst determine if the users are looking at advertisements or reading the content of a web page. However, little is known about the users' reactions besides how long users look at a certain location on the screen.

BRIEF DESCRIPTION OF THE DRAWINGS

Features and advantages of embodiments of the present invention will become apparent from the appended claims, the following detailed description of one or more example embodiments, and the corresponding figures, in which:

FIGS. 2(a) and (b) depict spatial distribution of cognitive load in an embodiment of the invention.

FIG. 3 depicts temporal distribution of cognitive load in an embodiment of the invention.

FIG. 7 includes a system for implementing embodiments of the invention.

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

An embodiment of the invention includes a system that tracks a user's pupillary response to content located on a document, such as a web page. The system then determines a cognitive load for the user that is based on the measured response. Cognitive load refers to the total amount of mental activity imposed on a user's working memory in any one instant. Further, the system may aggregate the cognitive load data for one user over time, for many different users, and/or for many different users over time. The cognitive load may be determined for different portions of a displayed page, such as a document object model (DOM) included on the page. The cognitive load may be specified for different elements that make up the DOM. Also, cognitive load may be apportioned over several different DOM elements at one moment in time or over a period of time.

Figure 1:
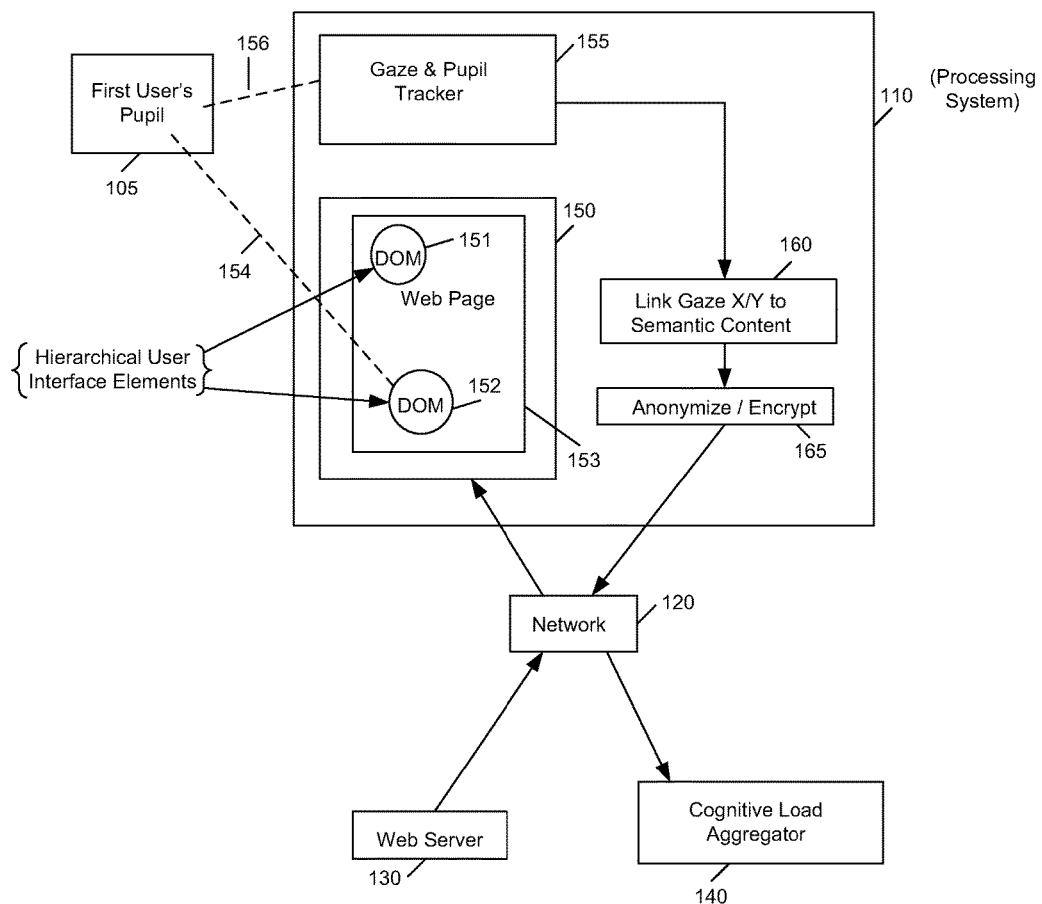
FIG. 1 includes a system and flow chart for an embodiment of the invention.

FIG. 1 includes a system and flow chart for an embodiment of the invention. System 100 includes processing system 110, such as the system of FIG. 7 described further below. System 110 may be included within, for example, a personal computer, server, laptop, mobile phone, tablet, and the like. System 110 couples, via a wireless or wired network 120, to a content provider such as web server 130. System 110 also couples, via network 120, to another processing unit such as server 140, which serves as a cognitive load aggregator. System 100 may be considered to include at least one processor, to process pupillary response, coupled to at least one machine accessible medium to store results of the processing. The units of system 100 (e.g., units 110, 120, 130, 140), including the at least one processor and at least one machine accessible medium, may be housed in a single chassis, in a distributed computing system, and the like.

System 110 may include display 150 to display web page 153, as provided from server 130. Web page 153 may include DOMs 151, 152. DOMs are discussed more specifically further below. To infer cognitive load for user 105, gaze tracker 155 may track the eye movement of user 105.

A gaze tracker, such as a T/X series eye tracker from Tobii Technology (www*tobii*com), may be used in an embodiment. A high resolution image of the eye gained by a gaze tracker may be used to measure relative change in pupil size. System 100 may correlate this pupillary response to cognitive load, including emotional reactions such as arousal. The value of measuring pupil response, and in turn inferring cognitive load, has many benefits. For example, the aggregated data may help an analyst understand which portions of a page (e.g., web page) are easier to read and which portions are more difficult to read. This capability may help in the analysis of an advertisement, as feedback to writers and publishers to improve the content they produce, and the like.

In an embodiment, gaze tracker 155 is included within unit 110 (e.g., in the laptop lid or tablet bezel) but in other embodiments, tracker 155 is merely coupled to (but not included in) unit 110 via a peripheral coupling. Gaze tracker 155 outputs an estimate of where the user is looking on the computer screen and the current size of the user's pupils. For example, a rendering engine may convert a DOM to pixels. Then, each element/branch in the DOM tree may have a position and size when rendered. Using the rendering information from the rendering engine, the system can associate a given X/Y value to the associated DOM elements.

Returning to FIG. 1, gaze tracker 155 may monitor (line 156) the user's eye 105 to determine X/Y coordinates for the user's line of site 154. In the example of FIG. 1 the X/Y coordinates align with DOM 152. In block 160, the X/Y coordinates are linked or coupled to semantic content, such as DOM 152. Unit 110 and/or unit 140 may perform this linking. Again, the at least one processor of system 100 may be distributed within system 100 and among units 110 and/or 140.

In block 165 data, whether merely composing X/Y coordinates or composing more processed data (e.g., including linking information to semantic content), may be "anonymized" whereby patient identification data is removed from content. The anonymized content may then be encrypted (e.g., using symmetric or asymmetric encryption protocols) and transferred to unit 140. Embodiments of the invention may leverage networked units 110, 120, 140 to build an aggregate model of cognitive load for multiple users viewing the same content.

Before proceeding, DOMs are described more fully. A DOM is an application programming interface (API) for documents, such as Hypertext Markup Language (HTML) and Extensible Markup Language (XML) documents. A DOM is a form of hierarchical user interface (UI) model that defines the logical structure of documents and the way a document is accessed and manipulated. With DOMs, the term "document" is used in a broad sense. For example, XML may be used as a way of representing many different kinds of information that may be stored in diverse systems, and much of this information would traditionally be seen as data rather than as documents. Nevertheless, XML presents this data as documents, and the DOM may be used to manage this data or document.

With a DOM, programmers can build documents, navigate the structure of the documents, and add, modify, or delete elements and content of the documents. For example, items found in an HTML or XML document can be accessed, changed, deleted, or added using a DOM. Thus, a DOM concerns how objects in a page (e.g., a web page having text, images, headers, links, and the like) are represented. A DOM defines what attributes are associated with each object, and how the objects and attributes can be manipulated. Dynamic HTML (DHTML) relies on a DOM to dynamically change the appearance of Web pages after those pages have been downloaded to a users browser.

A DOM allows a document (e.g., an HTML or XML document) to be represented as a hierarchical "tree" model. With a hierarchical UI model, such as a DOM, a tree model may provide hierarchical layers of roots, branches, leaves and the like. These layers are viewed relative to one another such that, for example, a leaf is a lower hierarchical level than a root. With a DOM, each document has a "root" or "root node" (top level node), which contains "children" or "nodes", which themselves can have children. The leaves contain the text of the document and have no children. These nodes are also referred to as "elements."

Thus, as used herein a DOM is defined broadly as a form of hierarchical UI model that describes the logical structure of documents and covers abstract hierarchical representations (i.e., models) of the content presented on the page.

Figure 4:
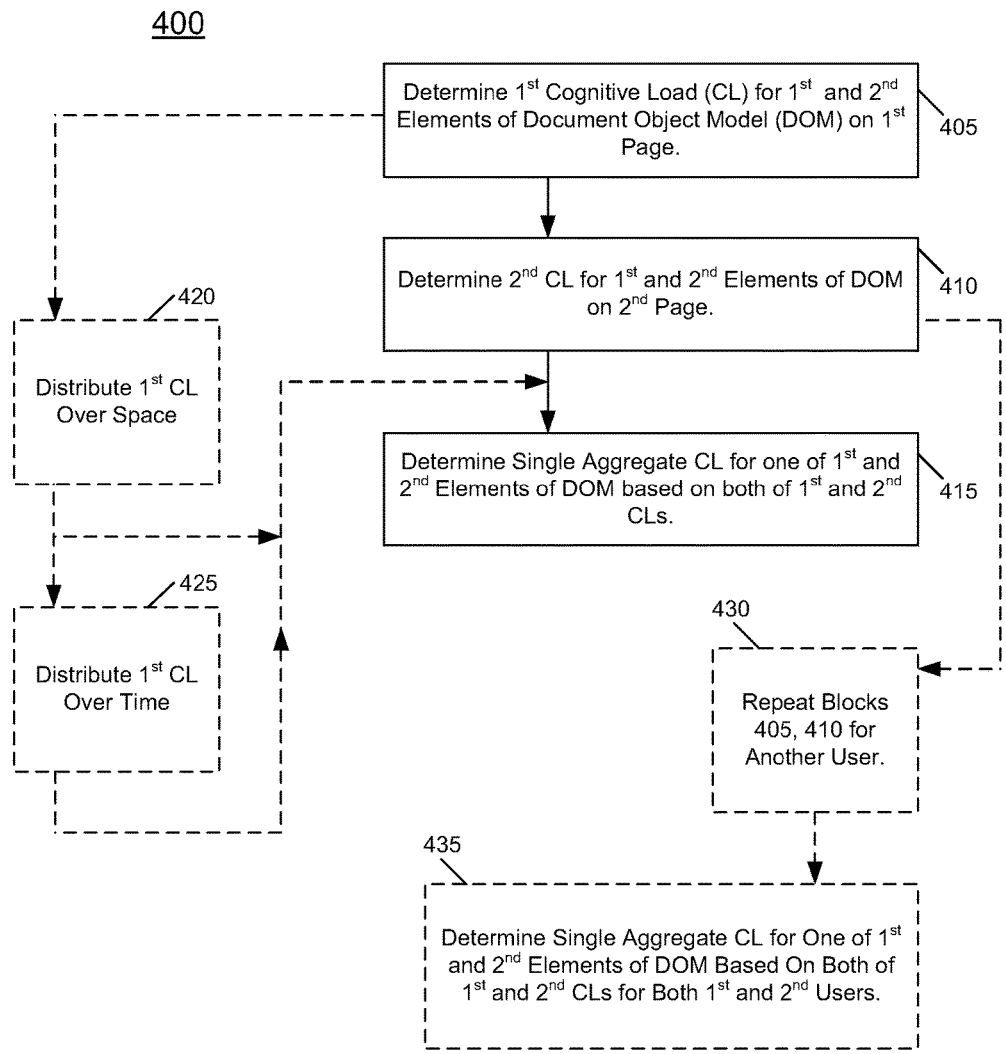
FIG. 4 includes a flow chart for a process in one embodiment of the invention.
Figure 5:
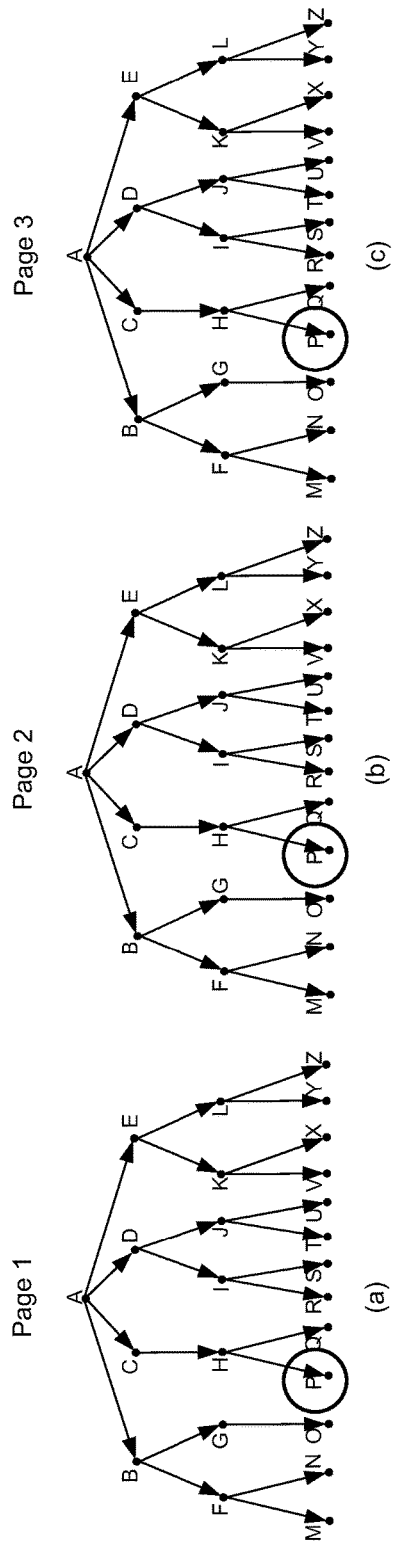
FIGS. 5(a), (b), and (c) depict cognitive load analysis per document object model element in an embodiment of the invention.

FIG. 5*a* includes a DOM. The DOM has root node A at the top hierarchical level, with four child node elements B, C, D, and E the second highest hierarchical level. The next hierarchical level includes child node elements F, G, H, I, J, K, L. The next hierarchical level includes "leaves" (which have no child nodes) M, N, O, P, Q, R, S, T, U, V, X, Y, Z. For example, the DOM of FIG. 5(*a*) may represent a table. Node or element A may include a <table> tag that defines a HTML table. Elements B, C, D, and E may each include a <tr> tag that defines a row in an HTML table. Elements F, G, H, I, J, K, L may each include a <th> tag that defines a header cell in an HTML table. Header cells may contain header information that provides for text that is bold and centered. M, N, O, P, Q, R, S, T, U, V, X, Y, Z may include text for the header cells. Discussion regarding FIG. 5 is provided in greater detail after discussion of FIGS. 2-4.

With the above overview of FIG. 1 and DOMs in mind, FIGS. 2-4 are collectively addressed.

FIG. 4 includes a flow chart for a process in one embodiment of the invention. Block 405 of process 400 includes processing a first user's pupil activity, using at least one processor (e.g., which could be located on unit 110, unit 140, a combination of units 110 and 140, and the like), to determine the first user's first cognitive load for first and second elements of a first hierarchical UI model (e.g., a DOM) included on a first page that displays the first and second elements in a first spatial orientation to one another.

FIG. 2*a* depicts a DOM with elements 1 through 16, all include in a first page. The elements may all be in the same hierarchical level or may span various hierarchical levels. The elements are arranged in a spatial orientation to one another. For example, element 6 is above element 10. FIG. 2*b* depicts the same DOM, however the DOM has been "reflowed" on this second page. Here, the elements are arranged in a spatial orientation to one another that differs from that of FIG. 2*a*. For example, element 6 is no longer directly above element 10.

Thus, block 405 determines the first user's (e.g., user 105 of FIG. 1) first cognitive load for first and second elements (such as elements 6 and 10) of a first DOM included on the first page of FIG. 2*a*.

Block 410 includes processing the first user's pupil activity, using the at least one processor, to determine the first user's second cognitive load for the first and second elements of the first DOM included on a second page that displays the first and second elements in a second spatial orientation to one another that is unequal to the first orientation. For example, the spatial orientation between elements 6 and 10 has changed from FIG. 2*a* to FIG. 2*b* because the first page of FIG. 2*a* has reflowed differently from the second page of FIG. 2*b*.

Process 400 may include storing the first user's first and second cognitive loads in at least one machine accessible medium coupled to the at least one processor. Again, the at least one medium could be located on unit 110, unit 140, a combination of units 110 and 140, and the like.

Block 415 includes determining a single aggregate cognitive load for one of the first and second elements (e.g., element 6, element 10, elements 6 and 10) of the first DOM based on both of the first user's first and second cognitive loads. Thus, for example, process 400 provides analysis for the cognitive load for element 6 in two different pages (FIGS. 2(*a*) and (*b*)) that have reflowed the DOM differently from one another. Various embodiments for determining aggregate cognitive load on a DOM element by element basis are described below.

Dotted lines and blocks of FIG. 4 help show options that may, partially or wholly, cooperate with other blocks of FIG. 4.

Block 420 includes an embodiment comprising attributing first and second portions of the first user's first cognitive load respectively to the first and second elements of the first DOM included on the first page. For example, in FIG. 2*a* the cognitive load is represented by the circle that reaches across elements 6, 7, 10, and 11. In an embodiment the cognitive load is distributed across those elements. Element 6 consumes 75% of the cognitive load, element 7 consumes 10% of the cognitive load, element 10 consumes 10% of the cognitive load, and element 11 consumes 5% of the cognitive load. As those same elements are reflowed across different pages, element 6 may be determined to retain the majority of the cognitive load while elements 7, 10, 11 diminish as they move away from element 6 based on page reflowing. Such a result would underscore the cognitive load that should be truly attributed to element 6. For example, on the second page (FIG. 2(b)) element 6 (as judged by the circle overlapping elements 6, 7, 11, and 12) consumes 65% of the cognitive load, element 7 consumes 10% of the cognitive load, element 11 consumes 15% of the cognitive load, and element 12 consumes 10% of the cognitive load.

Now, block 415 (in light of block 420) may determine the aggregate load for element 6 by calculating an average for element 6 as follows: [75% (FIG. 2(a))+65% (FIG. 2(b))]/2=70% aggregate cognitive load attributed to element 6. The aggregate cognitive load for element 6 could be compared with an aggregate cognitive load for another element, such as element 10: [10% (FIG. 2(a))+0% (FIG. 2(b))]/2=5% aggregate cognitive load attributed to element 10. Analysis for cognitive load could then delve the reasons why, for example, element 6 has a higher aggregate cognitive load than does element 10.

Block 425 (which may be conducted instead of or in cooperation with block 420) comprises attributing a first portion of the first user's first cognitive load to the first element of the first DOM included on the first page at a first time period; and attributing a second portion of the first user's first cognitive load to the first element of the first DOM included on the first page at a second time period that immediately follows the first time period. For example, in FIG. 3 circles 305, 310, 315, 320 represent the gaze of user 105 (and corresponding cognitive load) respectively at times T, T-1, T-2, and T-3. In such an example, gaze is distributed across time due to, for instance, temporal lag and uncertainty or accuracy of the gaze tracking equipment. Thus, circle 320 is attributed 20% of the cognitive load, block 315 is attributed 20% of the cognitive load, block 310 is attributed 50% of the cognitive load, and block 305 is attributed 10% of the load. Each of those attributions may be further analyzed. For example, circle 310 may be further parsed as showing X, Y, Z, and W percentages respectively for elements 5, 6, 9 and 10 (see block 420).

Distribution of cognitive load over time (block 425) and/or space (block 420) may be illustrated in different forms. For example, histograms may be used to illustrate how the cognitive load trails off from an element after a user's gaze initially leaves the element, and the like. Histograms may be used to show varying levels of confidence (e.g., probability distribution) regarding where the cognitive load is placed. For example, the cognitive load may be shown as a probability distribution over space (e.g., based on an error estimate for the gaze tracking hardware and the size of the user's foveal vision). That analysis may be divided up and assigned to varying DOM elements. Then, if the page is reflowed or changed there is still a mapping of cognitive load.

Regarding time distribution, calculating the cognitive load may require looking at changes in relative pupil size, and therefore may be based on several measurements. For example, pupil size at time1 judged in relation to pupil size at time2 would yield a change in pupil size and a change in cognitive load. Also, there may be a delay between the stimulus and the resulting change in state as measured by pupil response. Thus, because there are components that change over time distributing the cognitive load over time may help accommodate temporal ambiguity (FIG. 3) in a manner similar to how spatial ambiguity is handled (FIG. 2).

Thus, when blocks 420 and 425 are both included in an embodiment those blocks include attributing a first portion of the first user's first cognitive load to the first element of the first DOM included on the first page at a first time period; attributing a second portion of the first user's first cognitive load to the first element of the first DOM included on the first page at a second time period that immediately follows the first time period; attributing a third portion of the first user's first cognitive load to the second element of the first DOM included on the first page at the first time period; and attributing a fourth portion of the first user's first cognitive load to the second element of the first DOM included on the first page at the second time period that immediately follows the first time period.

Returning to the capacity of an embodiment to analyze cognitive load on a DOM element by element basis, FIGS. 5(a), (b), and (c) illustrate a single DOM on three different pages. By determining cognitive load on a "per element" basis one can track cognitive load to element P in each of the three pages respectively found in FIGS. 5(a), (b), and (c). Thus, the same content can be shown on many pages/sites (e.g., an advertisement) with a cognitive load metric that follows a DOM element across the pages.

Figure 6:
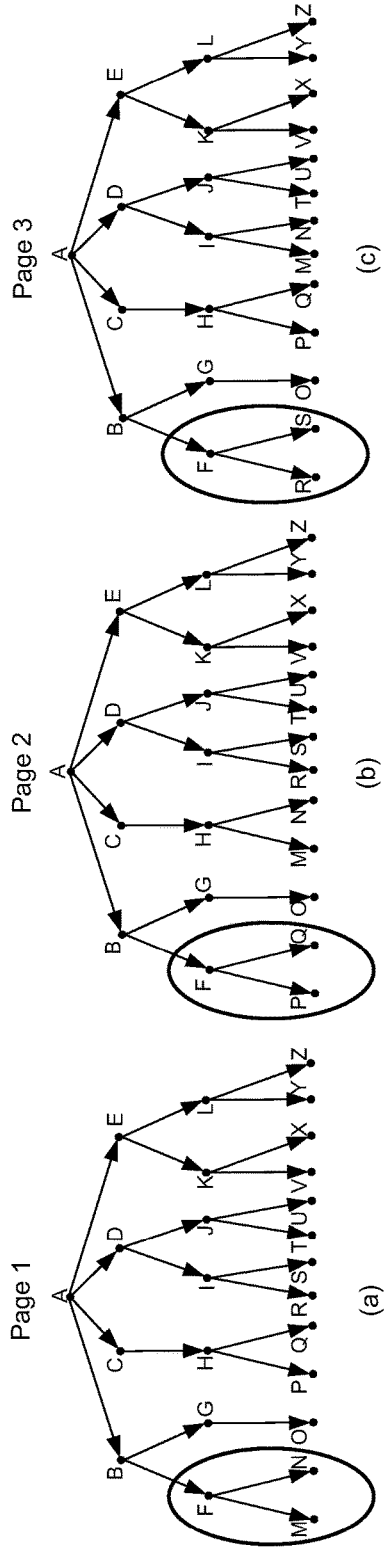
FIGS. 6(a), (b), and (c) depict cognitive load analysis per document object model branch in an embodiment of the invention.

FIGS. 6(a), (b), and (c) illustrate a single DOM on three different pages. However, while the top three hierarchical layers remain the same in each page, the fourth hierarchical layer changes. For example, for element F its child node elements change from elements M, N (FIG. 6(a)), to elements P, Q (FIG. 6 (b)), to elements R, S (FIG. 6(c)). Element F may constitute a radio button with content in leaves that changes from page to page (e.g., elements M, N, P, Q, R, S are leaves that include text). Thus, analysis can concern whether cognitive load of a user or users (aggregated or non-aggregated or one or more users) may be attributed to the radio button itself (element F) or the content (e.g., text) in the leaves of element F. In the example of FIGS. 6(a), (b), and (c) the circles indicate the cognitive load stays with radio button element F, regardless of the content associated with child node leaves.

FIGS. 6(a), (b), and (c) also show the same branch of a tree might be detached and reattached in a different place on a different page. For example, an advertisement is made up of a few DOM elements (a branch). That branch may be put in different places of the parent tree for different pages/sites. Cognitive load may now track the branch, instead of just a DOM in general or just with a page.

Returning to FIG. 4, optional blocks 430, 435 are now discussed. Block 430 includes repeating blocks 405, 410 (which were for a first user such as "user 1") but for another user such as "user 2" (and not user 1). Specifically, block 430 includes processing a second user's pupil activity, using the at least one processor, to determine the second user's first cognitive load for the first and second elements of the first DOM included on the first page. Block 430 further includes processing the second user's pupil activity, using the at least one processor, to determine the second user's second cognitive load for the first and second elements of the first DOM included on the second page. The block may also include storing the second user's first and second cognitive loads in the at least one machine accessible medium coupled to the at least one processor. Thus, a second user is now experiencing pages 1 and 2 of, for example, FIGS. 2a and 2b. Cognitive load analysis may again focus on any element, such as element 6 and/or element 10, despite the reflowing of the DOM in FIG. 2a versus FIG. 1a.

Block 435 includes determining a single aggregate cognitive load for one of the first and second elements of the first DOM based on both of the first user's first and second cognitive loads and further based on both of the second user's first and second cognitive loads. Thus, block 435 allows for an aggregate analysis of cognitive load for DOM element 6 as that element is reflowed across different pages and viewed by different users.

Regarding DOMs and FIGS. 2a and 4, first and second elements (e.g., elements 6 and 10) may each have a parent node and a child node. In such a case, neither of elements 6 and 10 are root node elements and neither of elements 6 and 10 are leaves. In an embodiment, each of the first and second elements may be included the same hierarchal level of the first DOM. For instance, elements 6 and 10 may each be <tr> tags that define rows in an HTML table. In other embodiments, the elements may be included in separate hierarchal levels of the first DOM. Element 6 may be a <tr> tag and element 10 may be a <th> tag. In fact, element 10 may be the child node of element 6 and element 6 may be the parent node of element 10. In still other embodiments, elements 6 and 10 may be leaf nodes that comprise text, thereby having a parent node but no child node.

In an embodiment, on the first page (e.g., FIG. 2a) the first element includes a first child node including first content and on the second page the first element includes a second child node including second content unequal to the first content. Thus, element 6 may be a <th> tag having a child node that says "10% Off Next Purchase" in FIG. 2a and "12% Off Next Purchase" in FIG. 2b. This is also illustrated with element F and its changing child nodes in FIGS. 6 (a), (b), and (c).

Also, returning to block 405 of process 400, which includes "processing" a first user's pupil activity, using at least one processor, to "determine" the first user's first cognitive load. Again, units 110 and/or 140 may perform this. Unit 110 may determine the cognitive load and send that value to unit 140. In such a case, unit 140 may still be said to be processing the pupil activity and determining the cognitive load by, for example, loading a cognitive load value into its memory.

Thus, various embodiments of the invention may interface with a web browser and determine the DOM component(s) the user is directing their view and concentration towards. Focusing on DOM elements, as opposed to a DOM in general or a page in general, may help analysis span different browsers that render the same information differently, or even the same browser that might reflow content differently based on window size. Likewise, a dynamic web page might show different users different content from the same page (e.g., different advertisements). Therefore, just noting the raw X/Y value for cognitive load may be less than ideal.

In an embodiment, the semantic information about what the user is looking at is bundled with the measure of pupil dilation or an inferred cognitive load estimate. This data could go through an optional anonymization and encryption stage (e.g., block 165 of FIG. 1) and then be sent over the network to a server. That server could be the originator of the content (e.g., the host of the web page, advertisement provider, and the like) or potentially a third party. In the cloud, the data may be aggregated and analyzed across many people. For example, simple statistics (such as the mean and variance) about the cognitive load for an advertisement may be computed. More advanced data mining techniques may be applied comparing competing content and optimizing for cognitive load. Aggregating via cloud based protocols allows for scaling analysis across many different users. Cognitive load results may be displayed via heat maps and the like. Further, gaze tracking may be conducted using web cams as well as devices dedicated to gaze tracking.

While many examples herein concern DOMs, other embodiments are not so limited and extend more generally to hierarchical UI models. Hierarchical UI models include hierarchical layers (e.g., roots, branches, leaves) to relate elements to one another. The models define the logical structure of documents and the way the document can be accessed and manipulated.

Also, various embodiments include processing pupil activity to determine cognitive load. This may include calculating the cognitive load at a first node (e.g., block 140) based on data acquired via a processing system (e.g., node 110 that is located remotely from the first node (e.g., via internet). However, processing pupil activity to determine cognitive load may also include receiving the cognitive load at node 140 from processing system 110 after the cognitive load was already calculated on processing system 110.

Embodiments may be implemented in many different system types. Referring now to FIG. 7, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multicore processors. The term "processor" may refer to any device or portion of a device that processes electronic data from registers and/or memory to transform that electronic data into other electronic data that may be stored in registers and/or memory. First processor 570 may include a memory controller hub (MCH) and point-to-point (P-P) interfaces. Similarly, second processor 580 may include a MCH and P-P interfaces. The MCHs may couple the processors to respective memories, namely memory 532 and memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces. Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Code may be included in one or more memories including memory 528, 532, 534, memory coupled to system 500 via a network, and the like. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. The terms "code" or "program" cover a broad range of components and constructs, including applications, drivers, processes, routines, methods, modules, and subprograms and may refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered. In one embodiment, use of the term control logic includes hardware, such as transistors, registers, or other hardware, such as programmable logic devices (535). However, in another embodiment, logic also includes software or code (531). Such logic may be integrated with hardware, such as firmware or micro-code (536). A processor or controller may include control logic intended to represent any of a wide variety of control logic known in the art and, as such, may well be implemented as a microprocessor, a micro-controller, a field-programmable gate array (FPGA), application specific integrated circuit (ASIC), programmable logic device (PLD) and the like.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. At least one storage medium having instructions stored thereon for causing a system to perform a method comprising:
    storing a first user's pupil activity data in the at least one storage medium, the first user's pupil activity data being derived from digital images that were captured by gaze tracker hardware;
    processing the first user's pupil activity data, using at least one processor, to determine a first attribution of the first user's pupil activity data to first and second elements of a hierarchical user interface (UI) model included on a previously displayed digital first page that displays the first and second elements in a first spatial orientation to one another;
    processing the first user's pupil activity data, using the at least one processor, to determine a second attribution of the first user's pupil activity data to the first and second elements included on a previously displayed digital second page that displays the first and second elements in a second spatial orientation to one another that is unequal to the first orientation;
    determining a single aggregate attribution of pupil activity data for one of the first and second elements, but not an additional one of the first and second elements, based on both of the first and second attributions of the first user's pupil activity data;
    determining an additional single aggregate attribution of pupil activity data for the additional one of the first and second elements based on both of the first and second attributions of the first user's pupil activity data; and
    attributing first and second portions of the first attribution of the first user's pupil activity data respectively to the first and second elements included on the first page,
    wherein (a) the first UI model includes a first document object model (DOM) and both of the first and second elements are included in a single hierarchal level of the first DOM, (b) each of the first and second elements has a parent node and a child node; and (c) the first and second portions correspond to a first instance of time.

2. The at least one medium of claim 1, the method comprising:
    processing a second user's pupil activity data, using the at least one processor, to determine a first attribution of the second user's pupil activity data to the first and second elements included on the first page;
    processing the second user's pupil activity data, using the at least one processor, to determine a second attribution of the second user's pupil activity data to the first and second elements included on the second page;
    storing the first and second attributions of the second user's pupil activity data in the at least one storage medium coupled to the at least one processor; and
    determining the single aggregate attribution of pupil activity data based on both of the first and second attributions of the first user's pupil activity data and further based on both of the first and second attributions of the second user's pupil activity data.

3. The at least one medium of claim 1, wherein:
    processing the first user's pupil activity to determine the first attribution of the first user's pupil activity data includes one of (a) calculating the first attribution of the first user's pupil activity data based on data acquired via a processing system, and (b) receiving the first attribution of the first user's pupil activity data from the processing system after the first attribution of the first user's pupil activity data was calculated on the processing system.

4. The at least one medium of claim 1, wherein on the first page the first element includes a first child node including first content and on the second page the first element includes a second child node including second content unequal to the first content.

5. The at least one medium of claim 1, the method comprising:
    attributing an additional portion of the first attribution of the first user's pupil activity data to the first element of the first UI model included on the first page at a second instance of time that immediately follows the first instance of time.

6. The at least one medium of claim 1, the method comprising:
    attributing an additional first portion of the first attribution of the first user's pupil activity data to the first element of the first UI model included on the first page at a second instance of time that immediately follows the first instance of time;
    attributing a third portion of the first attribution of the first user's pupil activity data to the second element of the first UI model included on the first page at the first instance of time; and attributing an additional third portion of the first attribution of the first user's pupil activity data to the second element of the first UI model included on the first page at the second instance of time.

7. An apparatus comprising:
at least one processor;
control logic, coupled to the at least one processor, to:
store a first user's pupil activity data in at least one machine accessible medium coupled to the at least one processor, the first user's pupil activity data being derived from digital images that were captured by gaze tracker hardware;
process the first user's pupil activity data, using the at least one processor, to determine a first attribution of the first user's pupil activity data to first and second hierarchical elements of a first hierarchical user interface (UI) model included on a previously displayed digital first page that displays the first and second elements in a first spatial orientation to one another;
process the first user's pupil activity data, using the at least one processor, to determine a second attribution of the first user's pupil activity data to the first and second elements included on a previously displayed digital second page that displays the first and second elements in a second spatial orientation to one another that is unequal to the first orientation;
determine a single aggregate attribution of pupil activity data for one of the first and second elements of the first UI model, but not an additional one of the first and second elements, based on both of the first and second attributions of the first user's pupil activity data; and
determine an additional single aggregate attribution of pupil activity data for an additional one of the first and second elements based on both of the first and second attributions of the first user's pupil activity data; and
attribute first and second portions of the first user's first attribution of the first user's pupil activity data respectively to the first and second elements included on the first page,
wherein (a) the first UI model includes a first document object model (DOM) and both of the first and second elements are included in a single hierarchal level of the first DOM, (b) each of the first and second elements has a parent node and a child node; and (c) the first and second portions correspond to a first instance of time.

8. The apparatus of claim 7, wherein the control logic is to:
process a second user's pupil activity data, using the at least one processor, to determine a first attribution of the second user's pupil activity data to the first and second elements included on the first page;
process the second user's pupil activity, using the at least one processor, to determine a second attribution of the second user's pupil activity data to the first and second elements included on the second page; and
determine the single aggregate attribution of pupil activity data based on both of the first and second attributions of the first user's pupil activity data and further based on both of the first and second attributions of the second user's pupil activity data.

9. The apparatus of claim 7, wherein on the first page the first element includes a first child node including first content and on the second page the first element includes a second child node including second content unequal to the first content.

10. The apparatus of claim 7, wherein the control logic is to:
attribute an additional portion of the first attribution of the first user's pupil activity data to the first element of the first UI model included on the first page at a second instance of time that immediately follows the first instance of time.

11. The apparatus of claim 7, wherein the control logic is to:
attribute an additional first portion of the first attribution of the first user's pupil activity data to the first element of the first UI model included on the first page at a second instance of time that immediately follows the first instance of time;
attribute a third portion of the first attribution of the first user's pupil activity data to the second element of the first UI model included on the first page at the first instance of time; and
attribute an additional third portion of the first attribution of the first user's pupil activity data to the second element of the first UI model included on the first page at the second instance of time.

* * * * *